United States Patent [19]
Urso

[11] Patent Number: 5,783,034
[45] Date of Patent: Jul. 21, 1998

[54] LINT, PET HAIR, DEBRIS AND BUG SNATCHER

[76] Inventor: Charles L. Urso, 54 Marivista Ave., P.O. Box 1136, Waltham, Mass. 02254

[21] Appl. No.: 722,978

[22] Filed: Sep. 30, 1996

[51] Int. Cl.⁶ .................................................. B32B 35/00
[52] U.S. Cl. ........................................ 156/579; 428/343
[58] Field of Search .................. 428/343; 15/104.002; 156/579

[56] References Cited

U.S. PATENT DOCUMENTS

| | | | |
|---|---|---|---|
| 2,671,917 | 3/1954 | Martin | 15/104.002 |
| 2,673,042 | 3/1954 | Fritzinger | 15/104.002 |
| 2,787,014 | 4/1957 | Barry | 15/104.002 |
| 2,854,682 | 10/1958 | Berezny | 15/104.002 |
| 3,066,342 | 12/1962 | Jackson | 15/104.002 |
| 3,089,170 | 5/1963 | Buchbaum | 15/104.002 |
| 3,430,496 | 3/1969 | Swanberg | 15/104.002 |
| 3,846,248 | 11/1974 | Rose | 15/104.002 |
| 4,083,075 | 4/1978 | Hester | 15/104.002 |
| 4,640,539 | 2/1987 | La Porte | 15/104.002 |

*Primary Examiner*—Jenna Davis

[57] ABSTRACT

A device for snatching arthropods and debris includes means for rotatably supporting a tape roll (20) having a sticky surface. First and second tape supports (8 and 33) support a span of the tape therebetween. Arthropods and debris are snatched on the sticky surfaced span wherein the tape can yield into space between the supports to avoid crushing the arthropods. A pivotally supported tape cutter (36) is provided for cutting off used tape portions. Guards (18) extending beyond the tape supports prevent the tape from contacting and sticking to smooth surfaces from which target arthropods may be snatched. A spring (29) urges the tape roll to rotate in a winding direction for yieldingly holding the tape span taut. A telescopically extendible handle (45) is connected for conveniently using the device in various applications. An adapter (50) having a resilient pad can be positioned so that the tape span is cushioned by the pad to conform to irregular surfaces of garments, upholstery, and carpets.

20 Claims, 3 Drawing Sheets

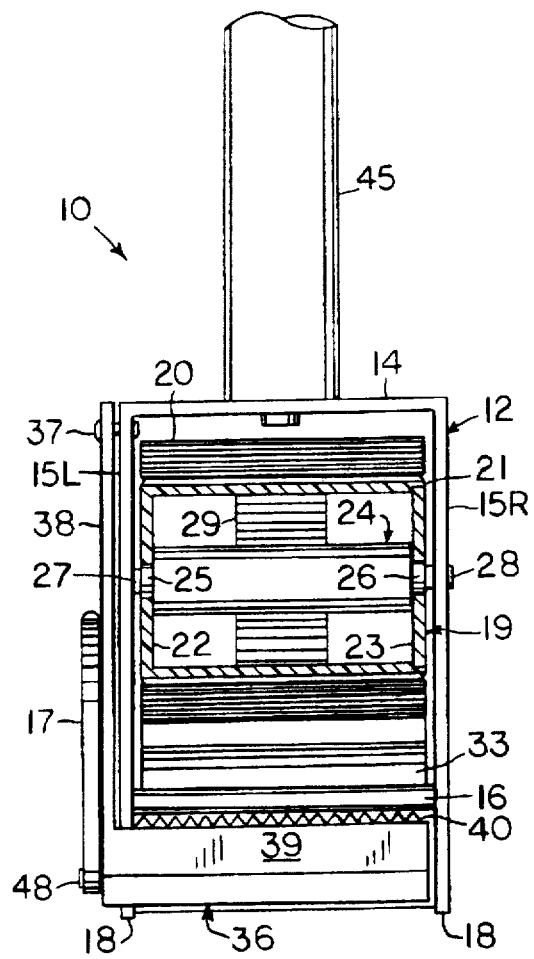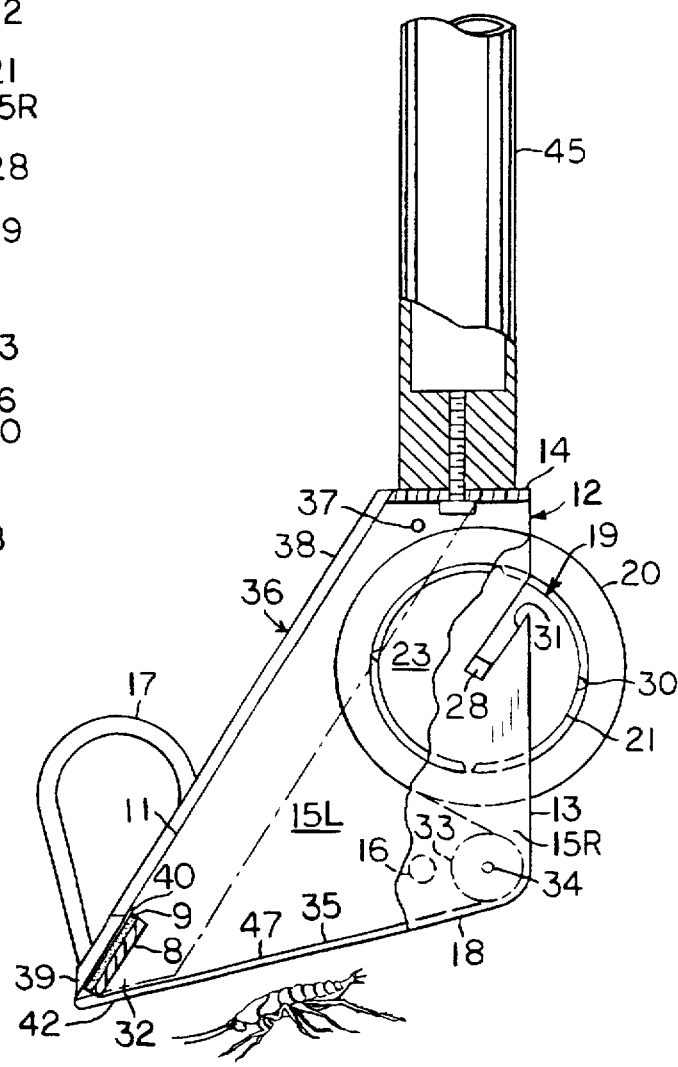
FIG. 1
FIG. 2

LINT, PET HAIR, DEBRIS AND BUG SNATCHER

TECHNICAL FIELD

This invention relates to devices for picking up lint, hair, debris, small objects and arthropods, and more particularly to devices that use tape having an adhesive and/or magnetic surface for doing so.

BACKGROUND

Unwelcome arthropods, including insects, arachnids, and myriapods frequently enter the dwellings of humans. Some types, such as scorpions, fire ants, certain spiders, and certain centipedes can severely sting or bite with added risk of infection to humans. Others, including roaches, can multiply in the home. Carpenter ants, large black ants commonly seen in the home during warm months, do a great deal of damage to the structure of a house. Moths lay eggs in closet clothing wherein the hatched larvae eat through the fabric.

When an arthropod is first seen in a house, it should be disposed of before it bites, stings, multiplies, or does damage. Picking the pest up by hand can be difficult and risky. Conventional methods of getting rid of the critter are usually messy. Smashing it with a rolled newspaper or swatting device leaves unsightly remains of the organism, including organic fluids and innards, on walls, ceilings, or furniture. Bug sprays leave potentially dangerous pesticide coatings in the house where children or pets could come in contact with the residue.

Getting a vacuum cleaner out is impractical every time a bug is seen; especially at remote locations in the home such as the attic or garage. Further, vacuum cleaners are too cumbersome and expensive to have at several convenient locations around the house or in the car. This inconvenience tends to make people ignore not only potentially damaging arthropods, but also small debris, such as lint, pet hair, or food crumbs until there is enough to justify getting the vacuum cleaner out. By not snatching up the debris immediately when first seen, however, the debris can spread and intermingle with the fibers of carpets and upholstery. Thus, the debris is more difficult to access later.

There are existing devices for removing lint from clothing. A lint brush require a lot of effort to use and then the brush has to be cleaned. There also are lint removing rollers resembling little paint rollers having a sticky surface on the roller. Exemplary lint rollers are disclosed by Wolfrum U.S. Pat. No. 4,427,726, Riboud U.S. Pat. No. 3,417,418, and Ramelson U.S. Pat. No. 3,343,194. Lint rollers have serious limitations because the surface in contact with the target surface at any given time is linear and too narrow to pick up debris other than flexible strands and fine particles. They lack a broad flat surface-to-surface contact for picking up larger particles such as chaff and chaff-like debris. Another limitation of lint rollers is that they cannot conform to the uneven surfaces of garments, upholstery or carpets. Still another limitation of lint rollers is that replacement of adhesive surface sheets, even though provided in multiple layers, is expensive in the long run. Further, lint rollers are not suitable for snatching bugs and other arthropods; especially large ones. The roller will crush the critters and leave remains behind.

An object of the present invention is to provide a small, light, and simple to use device that can snatch up arthropods of all types and sizes cleanly without crushing or smashing them. Another object is for the device to also be used to snatch up lint, pet hair, dandruff, food crumbs, dirt, chaff, and other debris off of clothing, upholstery, screens, fabrics, carpets, and auto seats. A further object is for the device to have a broad sticky surface that can conform to uneven surfaces of garments and upholstery such as lapels, piping, welting, and fabric covered buttons. Hence, the device would have versatility in the home, office and car. Still another object is to form the device mostly of molded plastic to be an inexpensive product.

SUMMARY

The present invention provides a device for snatching arthropods and debris, including lint and pet hair. The device comprises a frame with means for rotatably supporting a roll of tape having a sticky surface. First and second tape supports are connected to the frame and spaced from each other for supporting a span of the tape in a flat condition therebetween such that the sticky surface faces outward of the frame. Arthropods and debris are snatched on the sticky surface wherein the tape can yield into the space between the supports to avoid crushing the arthropods. The frame and first support are shaped to form a narrow peak for supporting the tape at the peak for being inserted into confined locations to snatch debris and arthropods therein. The frame and first support define a void within the peak for allowing the tape to yield into the void to avoid crushing arthropods snatched approximately at the peak.

A cutter is provided for cutting off a tape portion after use so that a fresh tape portion can be advanced from the roll and supported by the tape supports. The cutter is supported for being movable relative to the tape supports between an open position for advancing the tape and a closed position for cutting the tape. Included in the cutter is a pivotally supported arm having a cutting blade connected transverse to the arm. A retractable handle is pivotally connected to the arm for being movable relative to the arm between a deployed position for operating the cutter and a retracted position lowering the profile of the snatcher for operation in confined locations. Pivotal axes of the arm and handle are transverse to each other in one preferred embodiment and parallel to each other in another preferred embodiment.

Guards having elongated ridges extending beyond the tape supports prevent the tape from contacting and sticking to smooth surfaces from which target arthropods may be snatched.

A spring urges the tape roll to rotate in a winding direction for yieldingly holding the tape span taut.

A telescopically extendible handle is connected to the frame for conveniently using the device in various applications.

A detachably connectable adapter having a resilient pad can be positioned behind the tape so that the tape span is cushioned by the pad to conform to irregular surfaces of garments, upholstery, and carpets for removing lint, pet hair, and debris therefrom.

BRIEF DESCRIPTION OF THE DRAWINGS

The accompanying drawings in combination with the description herewith, illustrate features and advantages of the invention. Like reference numerals in different views refer to the same parts. The drawings are intended to illustrate principles of the invention and are not necessarily to scale.

FIG. 1 is a front view, partly in section, of a preferred embodiment of a snatcher constructed in accordance with the invention, wherein a tape cutter is in a closed position.

FIG. 2 is a side view of the snatcher of FIG. 1, partly in section, with a portion of a lateral wall broken away.

DETAILED DESCRIPTION OF PREFERRED EMBODIMENTS

Figure 3:
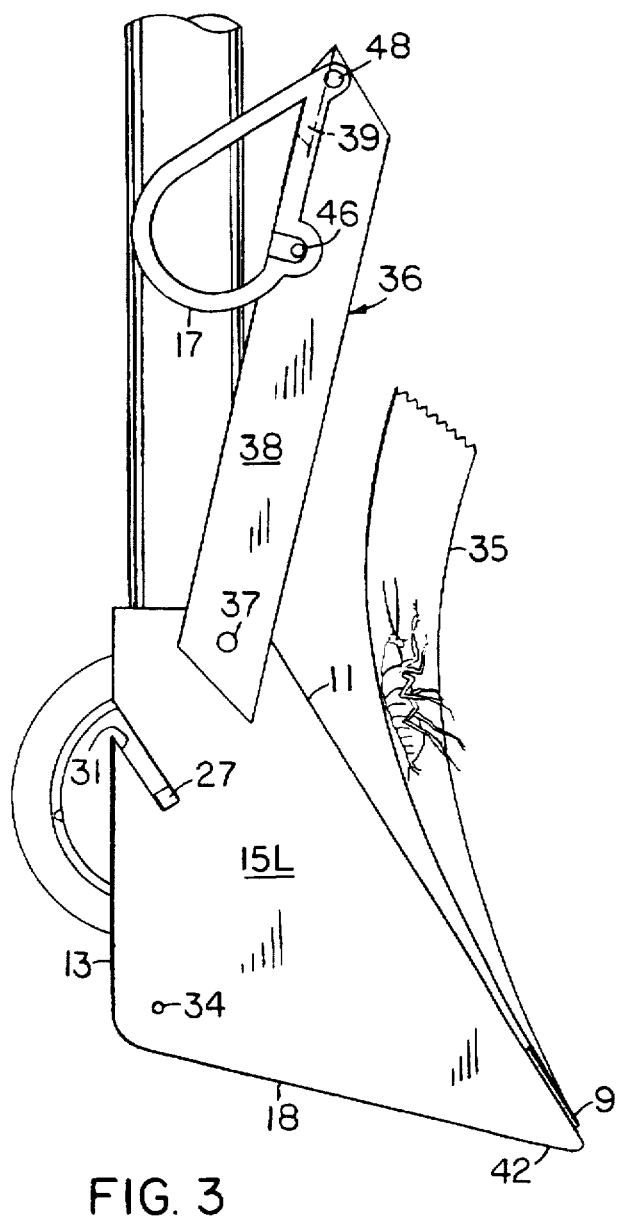
FIG. 3 is a side view of the snatcher of FIG. 1, showing an opposite side relative to that of FIG. 2, wherein the tape cutter is in an open position.

A preferred lint, pet hair, debris and bug snatcher embodying the principles of the present invention is shown in FIGS. 1-6 and is identified generally by reference numeral 10 in FIG. 1. Except as noted, the components of snatcher 10 are formed from molded plastic.

The snatcher 10 comprises a prism-shaped hollow housing or frame 12 having a rectangular top wall 14 and two lateral side walls 15L and 15R which are spaced parallel to each other. Walls 15L and 15R are aligned polygons substantially symmetrical to each other and rigidly connected by transverse supports which include wall 14, a post 16, and a narrow rectangular bridge or first tape support 8 (FIG. 2). Each wall 15L and 15R includes a leading edge 11, a trailing edge 13, and a base edge or guard 18. A narrow rectangular soft strip 9, made of rubber or urethane foam, is cemented onto an outer surface of support 8. The resilient surface of soft strip 9 is parallel to leading edges 11.

A conventional telescopically extendible hollow handle 45 (only a distal end portion is shown) is fixed to wall 14 by a screw passing through wall 14 and coaxially into handle 45.

A tape rotor 19 is supported between walls 15L and 15R for rotatably supporting a tape roll 20 of tape having a sticky surface. The term "sticky surface" herein is intended to include surfaces that are adhesive and/or magnetic to which objects will stick. Rotor 19 comprises a hollow cylindrical drum 21 which can be hand-pressed coaxially into the core of tape roll 20. Teeth 30 projecting from the rim of drum 21 ensure that drum 21 and tape roll 20 can only rotate together. Annular end caps 22 and 23 (FIG. 1) of drum 21 have central apertures for receiving respective inner end portions 25 and 26 of a plastic molded axle 24. Cross-sections of axle portions 25 and 26 are round so that drum 21 can rotate thereon. Outer end portions 27 and 28 of axle 24 have square cross-sections (FIGS. 2 and 3) for being received in respective slots 31 in walls 15L and 15R so that axle 24 cannot rotate.

Within drum 21, a torsion spring 29 (FIG. 1), encircling axle 24, has an inner end portion fixedly fitted in a slot (not shown) in axle 24. An outer end portion of spring 29 is urged against the inside of drum 21 thereby being friction connected thereto. Connected with a preset amount of friction, spring 29 and drum 21 form a slip clutch. Thus, when tape roll 20 and drum 21 rotate, spring 29 winds until the preset friction is overcome wherein drum 21 then slips about spring 29.

A roller or second tape support 33 is rotatably supported, between walls 15L and 15R, on a metal pin 34 (FIG. 2) which passes coaxially through support 33 and through aligned pin holes in walls 15L and 15R.

A tape cutter 36 (FIGS. 1-3), having an arm 38, is pivotally supported by a pin 37 which passes through an end portion of arm 38 and through a pin hole in wall 15L. As obvious, from the description and drawings, the pivotal axis of cutter 36 is parallel to the rotational axis of tape roll 20. Fixed perpendicularly to an opposite end portion of arm 38 is a transverse bar 39. A serrated metal cutting blade 40 is cemented transverse to arm 38 to an underside of bar 39 such that the teeth of blade 40 extend beyond a long edge of bar 39 and toward the pivotal axis of cutter 36. The cutter 36 is movable between a closed position (FIG. 2) for anchoring and cutting the tape, and an open position (FIG. 3) for advancing the tape. When cutter 36 is in the closed position, the resilient surface of soft strip 9 is opposite a smooth flat surface or tape anchoring surface of blade 40.

Figure 4:
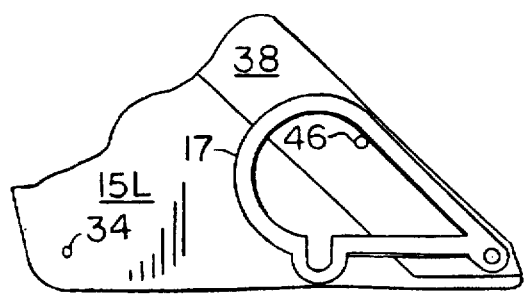
FIG. 4 is a fragmental side view of the snatcher of FIG. 1 showing the same side as that of FIG. 3, wherein the tape cutter is in the closed position and a loop handle of the cutter is retracted.

A retractable loop handle 17 is pivotally attached to arm 38 by a rivet 48 wherein handle 17 is movable between a deployed position (FIG. 3) and a retracted position (FIG. 4). A stop pin 46, projecting from arm 38 to within the loop of handle 17, prevents handle 17 from exceeding the retracted and deployed positions. The pivotal axis of handle 17 is parallel to the pivotal axis of arm 38.

Arm 38, pin 46, and bar 39 of tape cutter 36 are molded in plastic as a one-piece unit.

Operation of the Snatcher

As the components are arranged, a tape portion 35 shown in FIG. 2, is drawn from tape roll 20 thereby winding spring 29. While attached to roll 20, tape portion 35 is guided partway around support 33 to extend under support 8 and then between soft strip 9 and blade 40. The resilient surface of soft strip 9, opposite the anchoring surface of blade 40, evenly presses the sticky surface of the tape onto the anchoring surface. The tape interfacing and sticking to blade 40 anchors the tape span 47 between supports 8 and 33 such that the sticky surface of span 47 faces away from frame 12. Tape span 47 is at an acute angle with the anchoring surface of blade 40 and the resilient surface of soft strip 9. In addition, the span is yieldingly held taut by the tension of spring 29 which urges roll 20 in a winding direction. Tape span 47 forms a sticky window to snatch critters or debris.

With tape portion 35 under the tension of spring 29, tape roll 20 cannot slide out of slots 31. Thus, snatcher 10 can be turned upside-down to snatch critters from ceilings.

Guards 18 are positioned such that the elongated ridges of guards 18 extend beyond the tape supports 8 and 33. Hence, guards 18 prevent tape span 47 from contacting and sticking to smooth surfaces such as counter tops, floors, walls, or appliances while snatching critters. Tape span 47 will yield into the space between supports 8 and 33 to prevent the critters from being crushed so that no fragments or residue of insects or other arthropods are left behind. Frame 12 and first support 8 are shaped to form a narrow peak 42 for supporting the tape at peak 42 for being inserted into confined locations to snatch debris and arthropods therein. Frame 12 and support 8 also define a void 32 within peak 42 for allowing tape span 47 to yield into void 32 to avoid crushing arthropods snatched approximately at the peak 42.

If an arthropod being snatched is large, such as a scorpion, span 47 will wrap partway around the critter by drawing tape from roll 20 which will unwind as needed against the tension of spring 29. Hence, even large arthropods or other objects will not be crushed by the snatcher 10.

Loop handle 47 in the retracted position lowers the profile of the snatcher 10 wherein peak 42 is not impeded and may used to snatch critters in confined locations under low objects such as baseboard heaters, radiators, or appliances.

After use, tape span 47 may be replaced with a fresh span. A user can do so by holding tape roll 20 with one hand to prevent rotation. With the other hand, the user can pull on loop handle 17 (in the deployed position) to pivot tape cutter 36 to the open position (FIG. 3). Thus, blade 40 detaches from the sticky surface of the tape and leaves a loose tape end portion. The user can then pull on the loose tape end portion to draw a fresh span from roll 20. The used tape portion 35, in the position shown in FIG. 3, can be cut off by first moving the tape cutter 36 back to the closed position. By doing so, the flat anchoring surface of blade 40 compresses soft strip 9 with the tape therebetween. Soft strip 9, in turn, evenly presses the sticky tape surface onto the anchoring surface of blade 40 to anchor the tape span. Then, the user can pull the used tape portion 35 away from the snatcher 10 wherein the tape will be cut at the serrated edge of blade 40 and the device is ready for use.

To replace a tape roll, rotor 19 is first inserted coaxially into the tape roll core and then slipped into slots 31. The tape is advanced in the same manner as tape portion 35.

The snatcher 10 may also be used to snatch lint, pet hair, chaff, saw dust, food crumbs, and other debris off of clothing upholstery and carpets. The device is especially applicable for cleaning auto carpets and seats where debris is often present.

Figure 5:
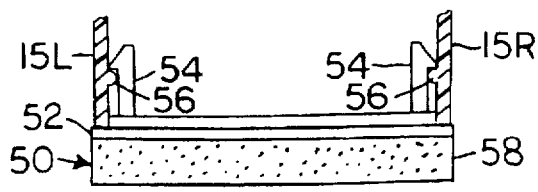
FIG. 5 is a front view of an adapter shown attached to a fragment of the snatcher of FIG. 1.
Figure 6:
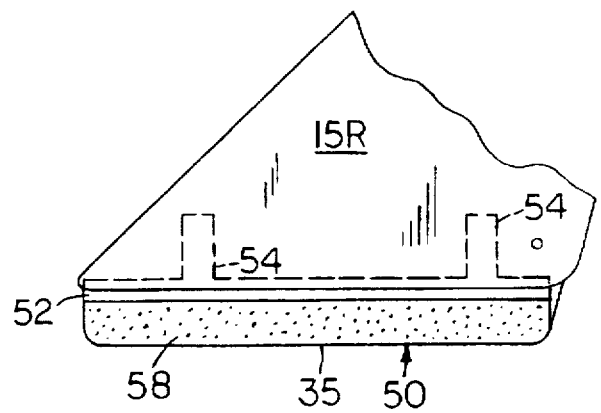
FIG. 6 is a side view of the adapter of FIG. 5 shown attached to a fragment of the snatcher of FIG. 1.

Shown in FIGS. 5 and 6 is a detachably connectable adapter 50 for enabling the most efficient use of the snatcher 10 on the fabric surfaces of garments, upholstery, and carpets. Included in adapter 50 is a rectangular plate 52 having stepped edges to mate with the base edges of walls 15L and 15R. Flexible catches 54, extending up from Plate 52, snap onto ridges 56 on the inside of walls 15L and 15R. Adapter 50 is attached by being pressed onto the underside of snatcher 10. The catches 54 and plate 52 are plastic molded as a one-piece unit. A sponge-like resilient foam pad 58, such as urethane or latex foam, is cemented to the underside of plate 52.

Tape portion 35 is positioned on the underside of pad 58 such that pad 58 is behind the tape with the sticky surface of the tape facing outward. Replacement of tape portion 35 with a fresh tape portion is done in the same manner as described hereinbefore, but with the tape span positioned outward of pad 58.

The resilient pad 58 allows tape 35 to conform to irregular or uneven contours, ridges, or implements on fabric surfaces for maximum performance. Thus tape 35, backed and cushioned by pad 58, conforms to garment lapels, zippers, piping, welting, ridges, fabric covered buttons, and coarse carpets to reach target lint, hair, or debris.

Figure 7:
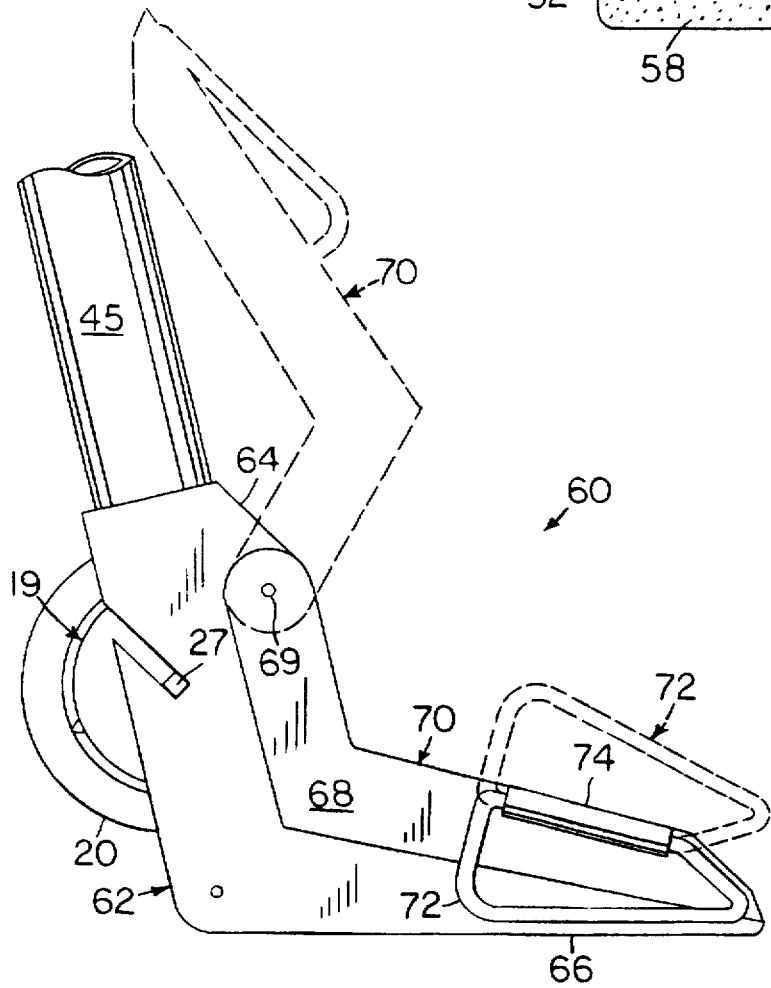
FIG. 7 is a side view of another preferred snatcher.

Another preferred snatcher is shown in FIG. 7 and is identified generally by reference numeral 60. The structure and components of snatcher 60 are the same as those of snatcher 10, but with the following modifications. The housing or frame 62 has an L-shaped profile wherein handle 45 is attached to the upper leg 64 of the L. A tape span (not shown), connected to tape roll 20, is supported in the lower leg 66 in the same manner as in snatcher 10.

To conform to the L-shaped frame 62, an arm 68 of a tape cutter 70 is also L-shaped and pivotally supported by a pin 69. Tape cutter 70 is movable between a closed position (solid tape cutter image) and an open position (phantom tape cutter image).

A loop handle 72 is pivotally supported in a ferrule 74 which is molded in plastic with tape cutter 70 as a one-piece unit. The pivotal axis of handle 72 is transverse to the pivotal axis of cutter 70 wherein handle 72 is movable between a retracted position (solid loop handle image) and a deployed position (phantom loop handle image). Tape cutter 70 is otherwise similar in construction, function, and operation as tape cutter 36 of snatcher 10.

The long low and tapered snout-like lower leg 66 of snatcher 60 enables the device to reach deeply under low objects such as furniture or machinery to reach critters or debris.

Available standard 2 inch wide tape rolls may be used in snatcher 10 or in snatcher 60. If clear plastic tape is used, the tape span forms a clear window through which target critters or objects can be seen. A user can look through the window and snatch the target precisely where preferred on the tape span. Though the clear window can be an added convenience, it is generally not necessary to look through it. Target objects can be caught anywhere on the tape span. Opaque biodegradable paper tape may also be used in the snatcher with great efficiency.

Special tapes for special applications of the snatcher are optional. Magnetic tapes may be used for selectively picking up iron or steel particles to separate them other small objects, for example. Or, magnetic tape combined with an adhesive coating may be used to broaden the range of target debris. Other types of tape with specific adhesive coatings designed for specific duties are among the options. For example, tape with a super-sensitive adhesive coating protected by a nonstick paper layer may be used. The nonstick paper layer may be torn off incrementally to expose the adhesive coating each time a fresh tape span is advanced from the tape roll in the snatcher.

While the above description contains many specificities, these should not be construed as limitations on the scope of the invention, but rather as exemplifications of preferred embodiments. Those skilled in the art will envision other possible variations that are within its scope. Accordingly, the scope of the invention should be determined not by the embodiments illustrated, but by the appended claims and their legal equivalents.

What is claimed is:

1. A device for snatching objects comprising:
   a handle;
   roll support means, connected to the handle, for supporting a roll of adhesive tape to rotate about a roll axis;
   tape support means, connected to the handle, for supporting a tape portion extending from the roll;
   a resilient pad positioned adjacent the tape support means such that the tape portion is backed and cushioned by the pad to conform to target objects thereby enhancing adhesion of the tape portion to target objects; and
   a tape cutter connected to the handle for cutting off tape after use wherein the tape cutter is supported for being movable relative to the tape support means between open and closed positions, in the closed position the cutter facilitates cutting the tape.

2. The device as defined in claim 1, wherein the tape cutter includes an anchoring surface for interfacing with the tape adhesive surface to anchor said tape portion.

3. The device as defined in claim 1, further comprising a resilient soft strip adjacent and cooperative with the cutter for pressing the tape onto an anchoring surface to anchor said tape portion when the tape cutter is in the closed position.

4. The device as defined in claim 1, wherein the tape cutter includes an arm pivotally supported for being movable about a pivotal axis which is approximately parallel to the roll axis, and a cutting blade fixed transverse to the arm.

5. The device as defined in claim 4, wherein the tape cutter includes a retractable handle connected to the arm for being movable relative to the arm between a deployed position for operating the cutter and a retracted position.

6. The device as defined in claim 5, wherein the retractable handle is movable about a pivotal axis which is parallel to the pivotal axis of the arm.

7. The device as defined in claim 1, wherein the tape cutter includes an arm supported to move about a pivotal axis, the arm supports a cutting blade having a cutting edge positioned transverse to the arm and directed approximately toward the pivotal axis.

8. The device as defined in claim 1, further comprising spring means for creating spring tension longitudinally on said tape portion.

9. The device as defined in claim 8, wherein the spring means includes a spring connected to the roll support means for urging the tape roll to rotate in a winding direction.

10. The device as defined in claim 1, wherein the tape cutter is supported to move about a pivotal axis and the cutter includes a serrated cutting edge having teeth directed approximately toward the pivotal axis.

11. A device for snatching objects comprising:

a frame;

roll support means, connected to the frame, for rotatably supporting a roll of adhesive surfaced tape;

a tape support, connected to the frame, for supporting a length of tape extending from the roll such that the adhesive surface faces away from the frame to snatch objects, the frame and tape support form a narrow peak for supporting the tape at the peak so that the peak can be inserted in confined locations to snatch objects therein.

12. The device as defined in claim 11, wherein the frame and first support define a void within the peak for allowing the tape to yield into the void to avoid crushing objects snatched approximately at the peak.

13. The device as defined in claim 11, further comprising a resilient pad connected to the frame for backing said length of tape to snatch small objects, and detaching means for expediently removing the pad therefrom in order to snatch relatively large objects by using said device.

14. The device as defined in claim 11, further comprising a slip clutch having a spring connected to the roll support means for urging winding rotation of the tape roll, the clutch allowing the tape roll to rotatably unwind by slippingly, overcoming the urging of the spring.

15. A device for snatching objects comprising:

a frame;

roll support means, connected to the frame, for supporting a roll of adhesive surfaced tape to rotate about a roll axis;

tape support means, connected to the frame, for supporting a length of tape extending from the roll such that the adhesive surface faces away from the frame to snatch objects; and a tape cutter for cutting tape, the cutter being connected to the frame and supported to pivot about a pivotal axis which is substantially parallel to the roll axis.

16. The device as defined in claim 15, wherein the tape support means forms a narrow peak to support the tape at the peak such that the adhesive surface faces outward therefrom so that the peak can be inserted in confined locations to snatch objects therein.

17. The device as defined in claim 15, wherein the tape cutter comprises an arm, and a cutting blade fixed transversely to the arm so that the cutter is structured for anchoring said length of tape and for facilitating cutting off used tape.

18. The device as defined in claim 15, wherein the tape cutter includes a serrated cutting edge having teeth directed approximately toward said pivotal axis.

19. The device as defined in claim 15, further comprising a spring connected to the roll support means for creating spring tension longitudinally on said length of tape.

20. The device as defined in claim 15, further comprising a resilient soft strip adjacent and cooperative with the tape cutter for pressing the tape onto an anchoring surface to anchor said length of tape when the cutter is in a closed position.

* * * * *